United States Patent [19]

Lee et al.

[11] Patent Number: 5,741,315

[45] Date of Patent: Apr. 21, 1998

[54] APPARATUS FOR RECEIVING TELEMETRY SIGNALS FROM ACTIVE IMPLANTABLE MEDICAL DEVICES

[75] Inventors: Chik Yam Lee, Arcueil; Herve Deschamp, Suresnes, both of France

[73] Assignee: ELA Medical S.A., Montrouge, France

[21] Appl. No.: 821,523

[22] Filed: Mar. 21, 1997

[30] Foreign Application Priority Data

Mar. 22, 1996 [FR] France ................................ 96 03607

[51] Int. Cl.$^6$ ...................................................... A61N 1/375
[52] U.S. Cl. ............................................................. 607/60
[58] Field of Search .................................. 607/32, 33, 60, 607/61

[56] References Cited

U.S. PATENT DOCUMENTS

| | | | |
|---|---|---|---|
| 4,494,545 | 1/1985 | Slocum et al. | 607/32 |
| 4,542,532 | 9/1985 | McQuilkin | 455/78 |
| 4,985,922 | 1/1991 | Kolbert | 380/59 |
| 5,562,714 | 10/1996 | Grguious | 607/60 |
| 5,630,835 | 5/1997 | Brownlee | 607/32 |

FOREIGN PATENT DOCUMENTS

| | | | |
|---|---|---|---|
| 0661077A1 | 7/1995 | European Pat. Off. | A61N 1/372 |
| 3936547A1 | 5/1991 | WIPO | H04B 5/00 |

OTHER PUBLICATIONS

Deschamps, et al. U.S. Patent Application No. 08/363,742.

*Primary Examiner*—William E. Kamm
*Attorney, Agent, or Firm*—Orrick, Herrington & Sutcliffe LLP

[57] ABSTRACT

A device for the reception of signals emitted by an active implanted medical device. The device has a signal collector coil for the reception of a magnetic induction which receives a useful signal component ($B_s$) emitted by the implanted device (26) and a parasitic signal component ($B_p$) of external origin. There is at least one collecting coil (12) wound on a first portion (14) of a magnetic circuit and at least one compensation coil (22) wound on a second portion (20) of the magnetic circuit, the two portions of the magnetic circuit belonging to a common magnetic element (16) and being configured in a manner such that, when the device is disposed in face of the implanted device, the collecting coil is essentially crossed one time by the magnetic induction field lines of the useful signal component ($B_s$) and the compensation coil is crossed essentially twice, in opposite direction, by the same magnetic induction field lines, thereby allowing to discriminate the useful signal component for improved signal to noise ratios and high speed data transmission.

13 Claims, 2 Drawing Sheets

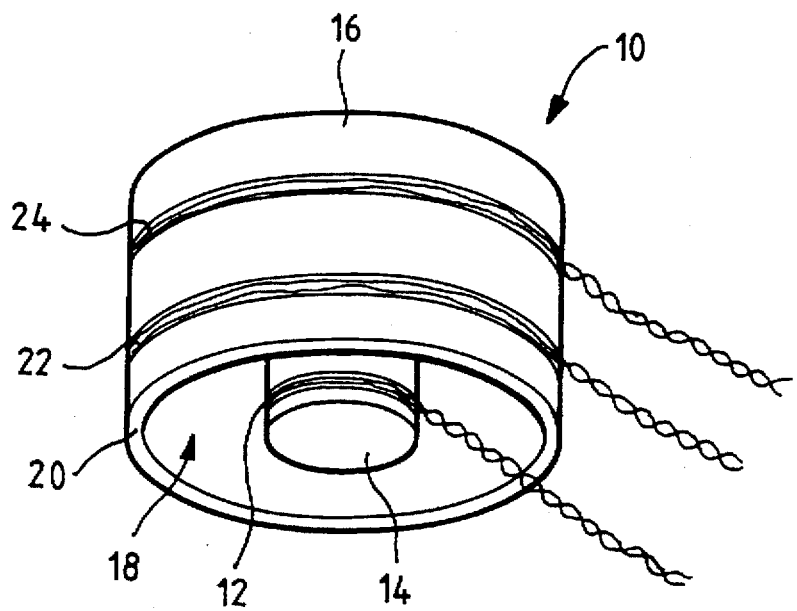
FIG_1
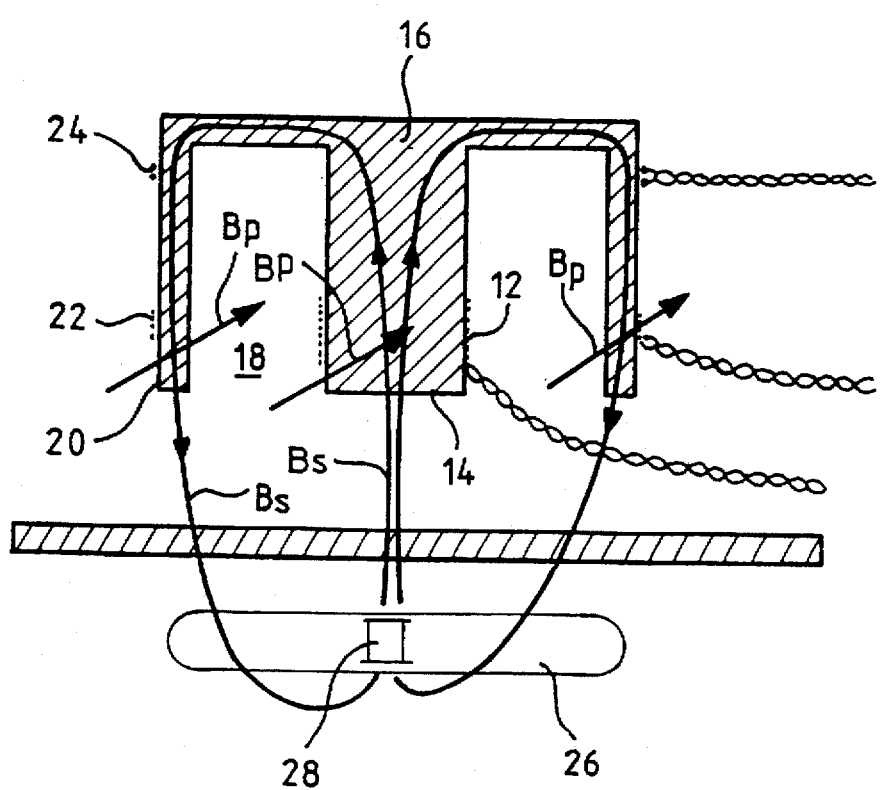
FIG_2

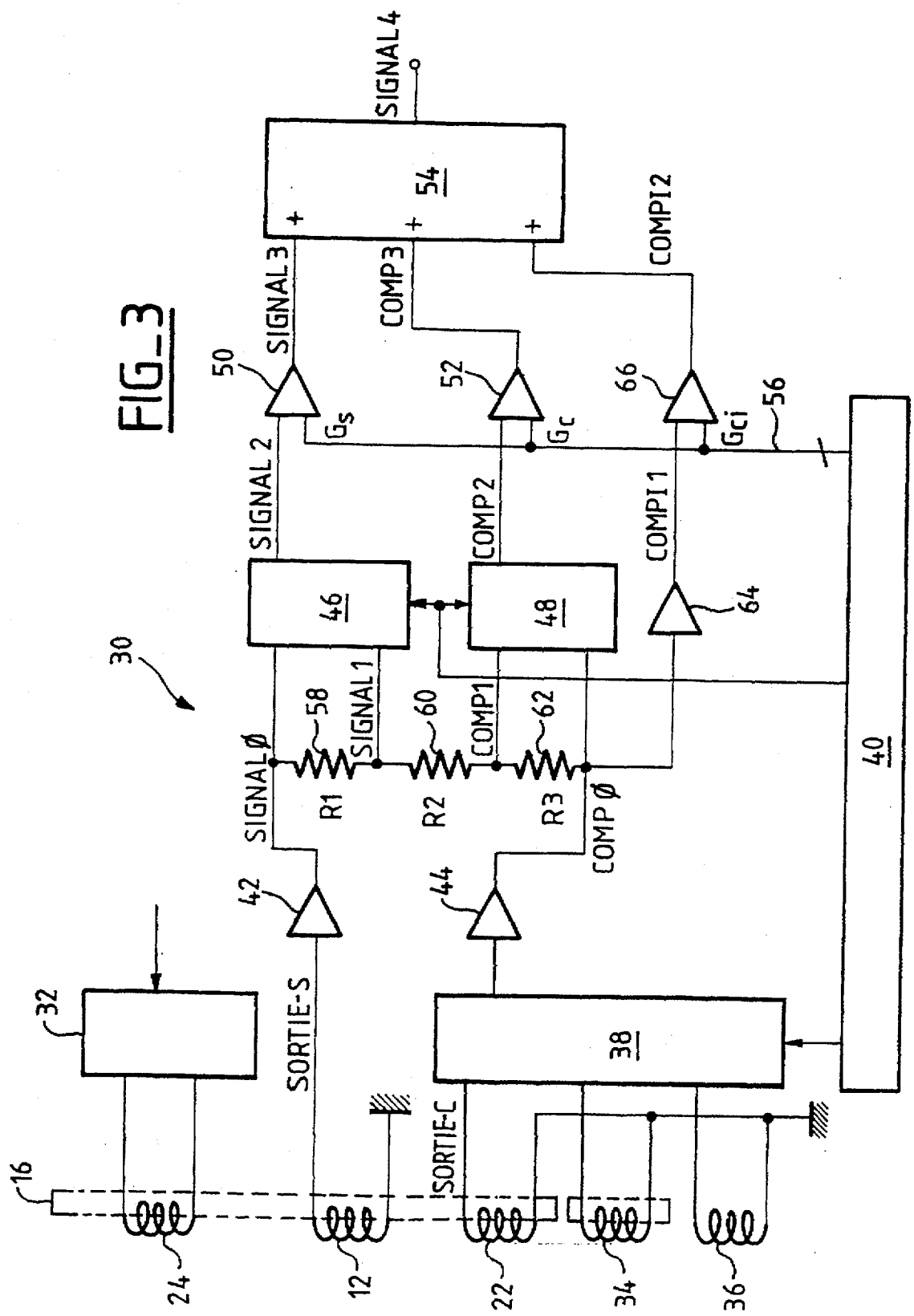
FIG_3

APPARATUS FOR RECEIVING TELEMETRY SIGNALS FROM ACTIVE IMPLANTABLE MEDICAL DEVICES

FIELD OF THE INVENTION

The present invention concerns implanted active medical devices, and more particularly the receipt of signals emitted during telemetry sequences of communication between the implanted device and an external control console or programmer.

BACKGROUND AND OBJECTS OF THE INVENTION

Active implanted medical devices notably comprise a class of devices including cardiac pacemakers, defibrillators, neurological devices, pumps for dispensing medical substances, and cochlear implants (collectively referred to as "implants"). These devices, once implanted, are typically programmed for operation from the exterior by means of a console called a "programmer".

The verification of the operating parameters of the implant or the transmission of information that has been or is to be recorded by the implant or the programmer is realized by electromagnetic coupling, called "telemetry" in the technique in question. Each programmer console is thus supplied with a receiver or "head" that is placed in the face of, that is, in proximity to the site of the implant. The head comprises a coil that records the magnetic field generated by the implanted device by which data is communicated.

The present invention has for its object an improvement to programmers that allows to increase, in notable proportions, the signal/noise ratio of the receiver head. The improvement of the signal/noise ratio is essential if one wishes to increase the speed of data transmission from the implant to the programmer. Indeed, the theoretical maximal speed of data transmission is linked essentially to the value of the signal/noise ratio of the transmission.

The average data transmission speed of a typical known implant device is on the order $1.5 \times 10^3$ bits per second in the direction from the implant to programmer. The quantity of data that can be transmitted from an implant during a telemetry session commonly reaches $8 \times 10^3$ bytes. This requires, therefore, with the speed of the known devices, a transmission time of 44 seconds.

The improvement brought about by the present invention allows, as one will see in the following discussion, to increase in considerable proportion this speed, in that one will be able to reach a transmission speed of typically $128 \times 10^3$ bits per second in the direction from the implant to programmer. As a result, the time required to transfer a block of $8 \times 10^3$ bytes of data is reduced to approximately 0.5 seconds, instead of the above-indicated 44 seconds with the known devices. This considerable and advantageous increase of speed, which is nearly two orders of magnitude, also allows to envision the transmission from the implant to the programmer, of much larger volumes of data, more particularly recordings of data that has been recorded over a very long period (as in the case of Holter recordings).

Thus, in the example of an endocardial ECG recording with a compression rate of 1:10, the quantity of data to transmit is $2.4 \times 10^6$ bits. With a classic known device, authorizing a transmission speed of only $1.5 \times 10^3$ bits per second, the transmission of this data would require approximately 27 minutes. In contrast, with a transmission speed of $128 \times 10^3$ bits per second, using an improved programmer and signal collection system in accordance with the present invention, only 19 seconds is needed to complete the data transmission.

It is known from EP-A-0 661 077 (ELA Medical) and its corresponding U.S. application Ser. No. 08/3633742 filed Dec. 23, 1994, which U.S. application is copending and commonly assigned and incorporated herein by reference, to increase the signal/noise ratio by combining signals recorded by a plurality of signal collectors and to operate a particular linear combination of signals delivered by the former in order to preserve essentially the useful component of the signal, and to eliminate the major part of noise components from parasitic sources.

It is nevertheless desirable to improve further on this technique, not only by reducing the noise by a particular signal combination collected by signal collectors, but also by collecting signals in order that the component of noise will have already been significantly reduced as a result of a particular signal collector geometry. One can thus obtain an improvement of the signal/noise ratio from the collection of signals, even before any processing of the signal by electronic circuits.

SUMMARY OF THE INVENTION

To this end, according to the present invention, a signal collector system that receives the signal emitted by an implanted active medical device, which comprises a means for collecting signals by the use of magnetic induction, the signals comprising a useful signal component emitted by the implanted device and a parasitic component of external origin, is characterized in that the signal collecting means has at least one collecting coil wound on a first portion of a magnetic circuit, and at least one compensation coil wound on a second portion of the magnetic circuit, these two portions of the magnetic circuit belonging to a common magnetic element and being configured in a manner such that, when the signal collecting means is disposed proximate to the implanted device, the collecting coil is essentially crossed once by the magnetic induction field lines from the useful component, and the compensation coil is essentially crossed twice, in opposite directions, by this same induction field.

In this manner, one collects at the compensation coil output a signal essentially representative of the parasitic component for combination with the signal collected at the output of the collecting coil.

In a preferred embodiment, the magnetic element is made of a material having a relative permeability greater than 1, comprising: a central core on which the collecting coil is wound; a peripheral ring on which the compensation coil is wound; and a central body connecting the core and ring in the region of magnetic element that is to be disposed furthest from the implanted device. The material of the magnetic element is more preferably a ferrite.

In one embodiment of the invention, it is foreseen that:

a first amplifier with an adjustable gain is provided to receive a signal output from the collecting coil;

a second amplifier with an adjustable gain is provided to receive a signal output from the compensation coil;

a summing circuit is provided to receive at its input the signals delivered by the first and second amplifiers, and to deliver at an output a resulting signal; and a control circuit to adjust the gains of the first and second amplifiers to obtain a difference between the signal from the compensation coil and the signal from the collecting coil in a manner to eliminate essentially from the collecting coil signal the parasitic component.

The elimination is made possible, by using the signal which originated from the compensation coil.

In this case, advantageously, signals applied on each of the first and second amplifiers are either signals proportional to signals collected by the respective coils, or signals corresponding to respective predetermined linear combinations of signals originating from the two coils. It also is foreseen to have a selection means for applying at the input of each of the first and second amplifiers, under the control of the control means, either signals proportional to signals collected by the respective coils, or respective predetermined linear combinations of signals coming from the two coils.

In another embodiment, an amplifier and integrator circuit is provided with an adjustable gain, receiving as an input the signal from the compensation coil, wherein the summing circuit also receives at its input the signal delivered by this amplifier and integrator circuit.

In yet another embodiment, the device comprises a plurality of compensation coils and means for selecting one of the plurality of compensation coils under the control of control means, thereby to obtain the best signal/noise performance.

BRIEF DESCRIPTION OF THE DRAWINGS

Other characteristics and advantages of the present invention will appear to a person of ordinary skill in the art in view of the following detailed description, made with reference to the drawings annexed, in which:

FIG. 1 is a perspective view, from the top, of a signal collector system according to a preferred embodiment of the present invention;

FIG. 2 is a cross-sectional view of the signal collector system of FIG. 1 illustrated proximate to an implant and showing the circulation of the magnetic induction field lines between the implant and signal collector system; and FIG. 3 is a schematic block diagram of a circuit for processing signals collected by the signal collector system of FIG. 2.

DETAILED DESCRIPTION OF THE DRAWINGS

Referring to FIGS. 1 and 2, the structure of a system of signal collectors (coils) of a programmer according to a preferred embodiment of the invention is shown.

It is generally known that, in the case of the telemetry of information from an implant, useful signals as well as parasitic signals are transported in the form of magnetic fields. The total signal received by a signal collector (i.e., a given coil) can be separated into a useful signal component $B_s$ and a parasitic signal component $B_p$. As described in the aforementioned EP-A-0 661 077 and corresponding U.S. application, it is possible to extract from the total signal the useful signal component by a particular linear combination of signals delivered by a plurality of distinct collecting coils, each having an induced magnetic flux and producing a corresponding voltage applied to a corresponding amplifier having variable gain, the respective outputs of which amplifiers are combined in a summing circuit.

The present invention proposes a particular geometry for these coils, as illustrated in FIGS. 1 and 2.

The system of signal collectors 10 comprises at least two coils, namely a so-called collecting coil 12, destined essentially to collect the useful signal, and one or more so-called "compensation" coils, destined to collect essentially a component of noise.

The collecting coil 12 is, in a characteristic manner of the invention, wound on the central core 14 of a half-pot (or open pot) 16 of ferrite, which component will be hereinafter designated for convenience by the word "pot". More precisely, the pot 16 is a classic pot (but deprived from its cover), having a relative permeability greater than 1, comprising a central cylindrical core 14 surrounded by an annular space 18 and a peripheral ring 20. The ensemble has, in radial section (FIG. 2), a general form of the letter "E", whose branches are turned to the exterior, that is to say in direction of the implant.

The invention is not, however, limited to the utilization of a ferrite in the form of a round pot, but it can be equally implemented by, for example, a square pot or another pot form, provided that the functional relative geometry of the different elements, such as will be explained hereinafter, is respected.

The compensation coil 22 is wound on the peripheral ring 20 of the ferrite pot.

The ferrite pot also carries an emission coil 24 serving for the transmission of signals from the programmer to the implant. It is, however, by convenience that this coil 24 is also disposed on the ferrite pot 16. Coil 24 does not participate in the reception of signals in accordance with the invention, and is therefore described here briefly only for completeness.

The ferrite used can advantageously be a soft ferrite of high magnetic permeability. It is generally known that high magnetic permeability materials have the ability to channel the flux of the magnetic induction provoked by close sources in relation to their geometry.

It is furthermore known that coils are the source of an electromotive force (current) when they are crossed by a magnetic induction varying in time. In particular, if the collecting coil 12 is crossed by an induction $B_s$ whose flux is $\Phi_s$, and that one calls OUTPUT-S (labeled SORTIE-S in figures), the representative signal of the electromotive force that is produced there by $\Phi_s$, is:

$$\text{OUTPUT-S} = -d\Phi_s/dt$$

The particular geometry of the invention allows, as one can see in FIG. 2, to place the ferrite pot 16 with coils 12 and 22 in face of the implant 26, that is proximate to the implant, when it is necessary to read information to be transmitted by the implant. The information is, for example, transported by the magnetic induction provoked by the passage of an oscillating current in the emitting coil 28 of the implant.

The induction $B_s$ produced by the passage of current in the emitting coil 28 has a tendency, if the signal collecting system is correctly positioned across from the implant, to enter in the ferrite 16 by the central part 14 and to emerge by the peripheral ring 20, with the magnetic field lines concentrating at the coil 28. The collecting coil 12 is going therefore to be crossed once and only once by the magnetic induction field lines $B_s$ produced by the emitting coil 28. On the other hand, the compensation coil 22 is going to be crossed twice, and in opposite directions, by these same field lines. As a result, the central collecting coil 12 will be essentially sensitive to signals emitted by the implant, while the peripheral compensation coil 22 will not be, or at least will be less sensitive to the implant emitted signals.

On the other hand, if sources of parasitic current provoke a parasitic induction $B_p$ at a distance (typically some tens of centimeters or more) from the ferrite pot 16, the direction of the parasitic induction $B_p$ will be less perturbed by the material of the ferrite pot 16, and this induction will cross in the same direction, and almost identically, the two coils 12 and 22. Thus, coils 12 and 22 that are therefore going to collect components of noise (parasitic components) that are appreciably identical.

The collected signals, that one will designate OUTPUT-S and OUTPUT-C (labeled SORTIE-S and SORTIE-C in FIG. 3), are then processed, by the circuit illustrated in FIG. 3, essentially in the manner described in aforementioned EP-A-0 661 077 and the corresponding U.S. application.

Reception circuits 30 of the programmer are schematically shown in FIG. 3 as including circuits of emission 32, discussed here for completeness only, that apply signals to the emission coil 24 to allow the communication of data from the programmer to the implant.

Although in the following the invention is described in the framework of a signal collecting system having two coils (a collecting coil 12 and a compensation coil 22), it is possible to foresee a larger number of coils, such as is taught in the aforementioned EP-A-0 661 077, for example, by installing auxiliary compensation coils 34, 36 (FIG. 3) which can be substituted, by means of a multiplexor 38 controlled by an appropriate control logic 40, to the main compensation coil 22 and function to collect signals. It should be appreciated that the terms "coil", "antenna" and "signal collector" in the context of the present invention are used interchangeably.

Thus, for example, it is possible to realize selectively a test of the functioning of the programmer with each of the possible compensation coils, and then to choose the one that in the given telemetry session allows one to realize the best processing of the signal, that is to say that obtains the best signal/noise ratio. It thus may be that in different telemetry sessions different compensating coils may be selected.

It is known, as taught in EP-A-0 661 077, that a linear combination of two signals, of the kind OUTPUT-S and OUTPUT-C, collected respectively at the output of coils 12 and 22 (or 34 or 36 if one uses auxiliary compensation coils), permits one to obtain a signal comprising as the sole component the useful signal component. Indeed, if one calls $S_u(t)$ the useful signal, and $S_p(t)$ the parasitic signal, and one writes:

OUTPUT-S=$\alpha S_u(t)+\beta S_p(t)$

OUTPUT-C=$\gamma S_u(t)+\delta S_p(t)$ then, by manipulation of the terms the expression obtained is:

OUTPUT-S–$\delta/\beta$ (OUTPUT-C)=$(\alpha-\gamma\delta/\beta) S_u(t)$ which is a signal no longer comprising any parasitic signal. If, as one has already written it, the compensation coil is insensitive or quasi-insensitive to the signal, which corresponds to settings $\gamma=0$, and the linear signal combination will be equal to $S_u(t)$, restoring therefore the completely useful signal. One thus optimizes, from the collection of the signal, the level of the signal/noise ratio.

The signals OUTPUT-S and OUTPUT-C stemming respectively from the collecting coil and the compensation coil are first of all amplified by respective first and second amplifiers 42 and 44, to give signals SIGNAL0 and COMP0. One operates then on these signals by a linear combination to produce a final signal free of parasites.

To this end, signals SIGNAL0 and COMP0 are applied, via multiplexors 46 and 48, whose role is explained below, to respective amplifiers 50 and 52, and then to a summing circuit 54. Amplifiers 50 and 52 are advantageously circuits incorporating digital converters, analog multipliers or digital potentiometers; and have respective gains $G_s$ and $G_c$ which are variable and controlled by a bus 56 transporting the values of the gains in digital form from the control logic circuit 40.

To realize the desired linear combination, one can use directly signals SIGNAL0 and COMP0. But, with a same number of bits defining gains $G_s$ and $G_c$ (for example, eight bits), one can realize a finer compensation of the parasitic signal by using for the linear signal combination signals SIGNAL1 and COMP1 derived from SIGNAL0 and COMP0 by the resistor divider bridge formed with resistances 58, 60 and 62, having respective values R1, R2 and R3 (preferably with R3=R1). Signals SIGNAL0 and COMP0 are to this end applied on the two extremities of the circuit formed of resistances R1 to R3 in series; the signal SIGNAL1 is then taken between resistors R1 and R2, while the signal COMP1 is taken from between resistors R2 and R3. This gives:

SIGNAL1=½ (SIGNAL0+COMP0)+(SIGNAL0−COMP0) (R2/(2R1+R2))

COMP1=½ (SIGNAL0+COMP0)+(SIGNAL0−COMP0) R2/(2R1+R2))

The choice of signal SIGNAL2 and COMP2 that will be applied to the amplifiers 50 and 52 is realized, respectively between SIGNAL0 and SIGNAL1 or COMP0 and COMP1, by the multiplexors 46 and 48.

After optimization of gain $G_s$ and $G_c$ and selection by the multiplexors 38, 46 and 48 of the combination of signals producing the best signal/noise ratio, the level of parasites will be identical on signal SIGNAL3 and COMP3 stemming from amplifiers 50 and 52, and the sum of these signals by the summing stage 54 will allow to obtain a signal SIGNAL4 comprising solely the useful signal component.

Nevertheless, in some configurations where the level of parasites is very intense and where the dimension of the implant is relatively large, it is possible that the implant re-emits a part of the integrated parasitic signal temporally, due to the fact of induced currents originating in the external surface of the implant, which surface is generally formed of a shell of a metallic conducting material, e.g., titanium.

To cancel this component, one will sum to SIGNAL3 and COMP3 the integrated part COMPI2 of the parasitic signal COMP0. To this end, the signal COMP0 is applied to an input of an integrator 64 whose output signal COMPI1 is applied on an amplifier 66 with adjustable gain (of the same type as amplifiers 50 and 52) whose gain $G_{cI}$ is also adjusted by the control circuit 40.

Of course, the processing of signals collected by the collecting and compensation coils can be realized in different manners. For example, the circuits can be implemented by entirely analog circuits, or entirely digital circuits, or a hybrid of analog and digital circuits. In the case of digital circuits, it can be driven or not by the means of a software program controlling a microprocessor in performing the aforementioned functions. In particular, the control circuit 40 can advantageously comprise a microprocessor or calculator able to solve a linear equation system in a manner to deduce the value of the different gains to apply to the amplifiers to obtain the optimal signal to noise ratio.

One skilled in the art will appreciate that the present invention can be practiced by other than the described embodiments, which are presented for purposes of illustration and not of limitation.

We claim:

1. Apparatus for the reception of a signal emitted by an active implanted medical device (26) comprising a means for collecting a signal (10) having magnetic induction field lines for the reception of magnetic induction comprising a useful component ($B_s$) emitted by the implanted device and a parasitic component ($B_p$) of external origin, characterized in that the signal collectors means comprises at least one collecting coil (12) wound on a first portion (14) of a magnetic circuit and at least one compensation coil (22) wound on a second portion (20) of said magnetic circuit, the first and second portions of the magnetic circuit comprising a common magnetic element (16) and being configured in a manner such that, when the signal collection means is disposed proximate to the implanted device, the collecting coil is crossed once by the magnetic induction field line of the useful component ($B_s$) and the compensation coil is crossed twice, in opposite directions, by said same magnetic induction field lines.

2. The apparatus of claim 1, in which the magnetic element further comprises a pot (16) having a relative permeability greater than 1 comprising:

a central core (14) on which is wound the collecting coil (12);

a peripheral ring (20) on which is wound the compensation coil (22); and a central body connecting the core and ring at a region distal to the implanted device (26).

3. The apparatus of claim 1, in which the magnetic element material comprises a ferrite.

4. The apparatus of claim 1, in which the collecting coil has an output signal (SIGNAL2) and the compensation coil has an output signal (COMP2), further comprising:

a first amplifier (50) having an adjustable gain ($G_s$) receiving a signal (SIGNAL2) from the collecting coil and having an output signal (SIGNAL3);

a second amplifier (52) having an adjustable gain ($G_p$) receiving a signal (COMP2) coming from the compensation coil and having an output signal (COMP3);

a summing circuit (54) receiving at an input signals (SIGNAL3, COMP3) delivered by the first and second amplifiers and having an output signal (SIGNAL4); and a control circuit (40) operable to adjust the gains ($G_s$, $G_c$) of the first and second amplifiers to obtain a difference between the signal from the compensation coil and the signal from the collecting coil in a manner to essentially eliminate the parasitic component.

5. The apparatus of claim 4, in which the input signals (SIGNAL2, COMP2) applied to the first and second amplifiers further comprise respective signals (SIGNAL0, COMP0) that are proportional to signals collected by the respective collecting and compensation coils or respective predetermined linear combinations (SIGNAL1, COMP1) of signals coming from the collecting and compensation coils.

6. The apparatus of claim 5, further comprising means for selecting (46, 48) to apply at the input of each of the first and second amplifiers (50, 52), under the control of the control means (40), one of signals (SIGNAL0, COMP0) proportional to signals collected by respective collecting and compensation coils, and respective predetermined linear combinations (SIGNAL1, COMP1) of signals coming from the two collecting and compensation coils.

7. The apparatus of claim 4, further comprising an amplifier and integrator circuit (64, 66) having an adjustable gain (GCI) receiving at an input the signal (COMP0) from the compensation coil, wherein the summing circuit further comprises a summing input to receive the signal (COMPI2) output by said amplifier and integrator circuit.

8. The apparatus of claim 4, comprising a plurality of compensation coils (22, 34, 36) and means (38) for selecting one of the plurality of coil under the control of said control means (40).

9. A signal collecting system of a programmer for telemetry communications with an active implantable medical device, comprising a magnetic circuit having first portion, a second portion and a third portion, the third portion connecting the first and second portions;

a signal collecting coil wound on the first portion; and a first compensating coil wound on the second portion;

wherein the first portion is separated from the second portion by a distance, the distance being dimensioned according to the active implantable medical device so that any magnetic flux field lines emanating from the implanted medical device cross the signal collecting coil one time and cross the first compensating coil twice in opposite directions.

10. The system of claim 9 wherein the magnetic circuit first portion further comprises a central core, the magnetic circuit second portion further comprises an annular ring spaced around said central core, and the magnetic circuit third element comprises a base connecting the annular ring and the central core.

11. The system of claim 10 further comprising a second compensating coil wound on the annular ring, the first and second compensating coils being spaced apart.

12. The system of claim 11 wherein the first compensating coil has a first signal output and the second compensating coil has a second signal output, the system further comprising a multiplexor having a first input and a second input operatively connected to the first signal output and the second signal output respectively, a selection input to select one of the first and second inputs, and an output corresponding to the one selected input.

13. The system of claim 9 wherein the signal collecting coil further comprises a collected signal output and the first compensating coil further comprises a compensating signal output, the system further comprising:

a first amplifier having an adjustable gain and an input connected to the connected signal output and a first amplified output;

a second amplifier having an adjustable gain connected to the compensating signal output and a second amplified output;

a summing circuit having an input connected to the first and second amplified outputs, and an output corresponding to a sum of the first and second amplified outputs; and a control circuit connected to the first and second amplifiers operable to adjust the gains of the first and second amplifiers, thereby to obtain a difference between the compensating signal output and the collected signal output.

* * * * *

UNITED STATES PATENT AND TRADEMARK OFFICE
CERTIFICATE OF CORRECTION

PATENT NO.    : 5,741,315
DATED         : April 21, 1998
INVENTOR(S)   : Chik Yam Lee and Herve Deschamp It is certified that error appears in the above-identified patent and that said Letters Patent is hereby corrected as shown below:

Column 1,
Line 31, delete "allows to" and insert -- allows an -- therefor;
Line 32, delete "the signal/noise" and insert -- of the signal/noise -- therefor;

Column 4,
Line 44, delete "in face" and insert -- in the face -- therefor;

Column 5,
Line 2, delete "that are" and insert -- are -- therefor;

Column 7,
Line 34, delete "$G_p$" and insert -- $G_c$ -- therefor; and

Column 8,
Line 6, delete "coil" and insert -- coils -- therefor.

Signed and Sealed this

Twenty-first Day of June, 2005

JON W. DUDAS
*Director of the United States Patent and Trademark Office*